United States Patent
Bernhardt et al.

[11] Patent Number: 5,827,361
[45] Date of Patent: Oct. 27, 1998

[54] CARBON-CONTAINING FIGMENTS

[75] Inventors: Klaus Bernhardt, Gross-Umstadt; Reiner Vogt, Kranichstein; Gerhard Pfaff, Münster, all of Germany

[73] Assignee: Merck Patent Gesellschaft mit beschrankter Haftung, Darmstadt, Germany

[21] Appl. No.: 412,580

[22] Filed: Mar. 29, 1995

[30]    Foreign Application Priority Data

Mar. 30, 1994  [DE]  Germany .......................... 44 10 990.3
Oct. 1, 1994   [DE]  Germany .......................... 44 35 300.6

[51] Int. Cl.$^6$ .................................................. C04B 14/20
[52] U.S. Cl. .......................... 106/415; 106/416; 106/472; 106/474
[58] Field of Search ..................................... 106/415, 417, 106/474, 475, 491, 489, 436, 447, 446

[56]              References Cited

U.S. PATENT DOCUMENTS

| | | | |
|---|---|---|---|
| 4,076,551 | 2/1978 | Bernhard et al. | 106/291 |
| 4,755,229 | 7/1988 | Armanini | 106/417 |
| 5,271,771 | 12/1993 | Franz et al. | 106/474 |
| 5,356,471 | 10/1994 | Reynders | 106/415 |
| 5,501,731 | 3/1996 | Schmid et al. | 106/456 |

FOREIGN PATENT DOCUMENTS 2123783  6/1993  Canada .

*Primary Examiner*—Melissa Bonner
*Attorney, Agent, or Firm*—Millen, White, Zelano, & Branigan, P.C.

[57]              ABSTRACT

The invention relates to carbon-containing pigments having improved abrasion resistance and dispersibility and to their production.

11 Claims, No Drawings

CARBON-CONTAINING FIGMENTS

The present invention relates to carbon-containing pigments having improved abrasion resistance, to their production, and to their use.

It is known that special color effects can be achieved by incorporating carbon into pigments. Carbon-containing pigments are therefore used not only for pigmenting coatings, powder coatings, paints, printing inks, plastics and the like but also in cosmetic preparations. The prior art processes for producing these pigments, however, have in some instances appreciable disadvantages.

The hitherto only way of producing combinations of carbon-metal oxide mica pigments was to apply carbon from an aqueous suspension using suitable surface-active auxiliaries or by pyrolysis of organic compounds. DE-B-1 165 182 describes a complicated pyrolysis process in which the carbon is naturally merely deposited on the pigment surface. The disadvantage of the complicated pyrolysis process is no longer present in DE-C-2 557 796. In the process described there, first a substance is mixed with a carbon black dispersion. A metal salt solution is added under hydrolysis conditions to precipitate a carbon black-containing metal hydroxide layer on the substrate. The pigments thus produced are separated off and dried at 130°–150° C. However, the pigments thus produced are unsuitable for various purposes, since their abrasion resistance is inadequate. This property is extremely undesirable especially for incorporation into cosmetic preparations. Calcining the pigments at temperatures of 700°–900 ° C. under oxygen-free conditions improves the abrasion resistance (DE-A-4 104 846). In DE-A-4 125 134, carbon-containing compounds are pyrolyzed in the presence of metal oxide platelets or of metal oxide-coated plateletlike substrates under conditions under which the metal in the metal oxide is reduced.

In the prior art processes the precipitation of the carbon is not quantitative; that is, the carbon is to some extent present on the pigment in an agglomerated state, so that the pigments lack hiding power. The non-precipitated carbon has to be removed by sedimentation, which is time- and cost-intensive.

A further disadvantage is the frequently observed bleeding out of the carbon on suspension of the pigments in organic solvents for producing coating systems.

Furthermore, these pigments have a brownish tinge and show a pronounced loss of luster due to absorption and scattering phenomena involving the coarsely divided precipitated carbon agglomerates.

It is therefore an object of the present invention to produce carbon-containing pigments having improved abrasion resistance and bleeding resistance and high luster in a technically simple manner. This object is achieved by the present invention.

Surprisingly it was found that carbon-containing pigments having an improved abrasion resistance and special color effects are obtained on calcining substrates coated with one or more metal oxides and organic colloids at temperatures >700° C. under oxygen-free conditions. Decomposing the organic colloidal particles under inert conditions at temperatures above 700° C. provides a direct way of producing very finely divided carbon particles in the metal oxide layer, without agglomeration, in the desired amount.

The present invention accordingly provides carbon-containing pigments obtainable by pyrolysis of substrates coated with one or more metal oxides and colloidal organic particles and optionally with an organofunctional silane compound at temperatures >700° C. under oxygen-free conditions.

The present invention further provides a process for producing the carbon-containing pigments, characterized in that an aqueous substrate suspension is prepared and admixed simultaneously but separately with at least one hydrolyzable metal salt solution and with an aqueous organic colloid solution, the pH of the substrate suspension being maintained by simultaneous addition of a base or acid within a range which causes the metal salt to hydrolyze, and the substrate coated in this way optionally has added to it an organofunctional silane compound and/or an aqueous organic colloid solution, and the substrate coated in this way is separated off, washed, dried and calcined at temperatures >700° C. under oxygen-free conditions.

Suitable base substrates for the coating step include on the one hand opaque and on the other transparent non-platelet-like substrates. Also suitable are platelets and platelet-like substrates of mica, talc, kaolin, bismuth oxychloride, glass, $SiO_2$ or synthetic ceramic flakes, synthetic support-free platelets or other comparable materials. It is also possible to use metal platelets, for example, aluminum platelets or platelet-like metal oxides, for example, platelet-like iron oxide and mica coatings with colored or colorless metal oxides, alone or mixed in a single layer or in successive layers. These pigments, which are known as pearl luster pigments, are known, for example, from the German patents and patent applications 1 467 468, 1 959 998, 2 009 566, 2 214 545, 2 215 191, 2 244 298, 2 313 331, 2 522 572, 3 137 808, 3 137 809, 3 151 343, 3 151 354, 3 151 355, 3 211 602 and 3 235 017. Preferred substrates are sheet-silicates and also metal oxide-coated platelet-like materials.

The plateletlike substrates generally have a thickness between 0.1 and 5 $\mu$m and in particular between 0.2 and 4.5 $\mu$m. The extension in the other two dimensions is customarily between 1 and 250 $\mu$m, in particular between 2 and 200 $\mu$m.

To produce the carbon-containing pigments of the invention, first an aqueous suspension of the substrate is prepared. To this suspension there may be added a solution of at least one metal salt. This is followed by the simultaneous but separate addition of a further metal salt solution and of the organic colloid solution, while the pH of the reaction mixture is maintained by simultaneous addition of an acid or base within a range which causes the metal salt to hydrolyze. This precipitates the metal oxide on the substrate surface together with the colloid particles.

By varying the thickness of the doped metal oxide layer it is possible, in particular in the case of titanium dioxide-coated plateletlike substrates, to obtain any desired interference colors of the first or higher order.

To precipitate the metal salts it is possible to use any acid or base. The most suitable concentration and pH can be determined by routine experiments. Usually the pH, once set for the precipitation, is maintained throughout the precipitation step in order that uniform pigments may be obtained.

It is convenient to use the industrially readily accessible bases, for example NaOH, KOH or ammonia, or dilute mineral acids. Since the bases and acids only serve to change the pH, their nature is not critical, so that other acids and bases can be used as well.

After the separation, washing and drying of the substrates thus coated, the pigments are calcined at temperatures >700° C., preferably at 800°–850° C., under oxygen-free conditions, and the organic colloid particles decompose. The calcining temperature generally depends on the thickness of the precipitated layer; the calcining time can range from a few minutes to several hours, but preferably is between 20 and 120 minutes.

Suitable metal salts from which the hydroxides can be precipitated include all water-soluble salts which are hydrolyzable by bases or acids. Preference is generally given to alkaline hydrolysis. Suitable metal salts include in particular those of aluminum, titanium, zirconium, iron, chromium, nickel, cobalt and/or tin.

The individual process parameters for the coating/metal salt hydrolysis step are of a conventional kind and have been extensively described, for example in DE 2 557 796. All further parameters, for example particle size, metal salt concentrations, temperatures and preferred embodiments, can likewise be taken from DE 2 557 796.

If desired, the pigments of the invention can also be aftercoated.

The organic colloid particles are an essential part of the coating. All known organic colloids having particle dimensions $<10^{-5}$ cm can be used. Preference is given to using readily water-soluble colloidal organic particles, for example polysaccharides, starch, cellulose or gelatin and their derivatives. The proportion of colloid particles on the substrate surface is from 0.1 to 20% by weight, preferably from 0.5 to 10% by weight, based on the total pigment.

The pyrolysis under inert conditions decomposes the colloid in the metal oxide layer, leaving an extremely finely divided carbon having dimensions <5 nm. The carbon is present in the metal oxide layer in a uniform dispersion. Voids between the metal oxides are filled, resulting in an extremely compact carbon-metal oxide layer of high hiding power.

The carbon content of the metal oxide layer is controllable through the amount of colloidal particles applied to the substrate surface together with the metal oxide.

The proportion of carbon in the pigments of the invention is generally between 0.05 and 20% by weight, preferably between 0.5 and 10% by weight, and in particular between 0.1 and 5% by weight, based on the total pigment.

Owing to the different substrates, the weight proportion of carbon can vary greatly. As the carbon content increases, the pigment becomes more and more graphitelike in its luster.

No bleeding of carbon due to organic solvents is observed, which can be ascribed to the small carbon particle size. Furthermore, the pigments of the invention are notable for enhanced luster and also for high hiding power. They are also weathering-resistant and non-conductive.

To improve the photostability of pigments according to the present invention which comprise a titanium dioxide layer, it is advisable to coprecipitate a water-soluble cerium (III) compound during the titanium salt hydrolysis and the colloid precipitation.

The cerium(III) salt can be added to the titanium salt solution in solid form or in aqueous solution or be metered into the substrate suspension concurrently with but separately from the titanium salt solution and the colloid solution. Suitable cerium(III) compounds include in particular cerium(III) salts, preferably the halides, especially the chlorides. For instance, in the $TiO_2$ pigments of the present invention, a cerium(III) content of 0.1–20% by weight, preferably 0.1–10% by weight, particularly 0.1–5% by weight, based on the total pigment, has proved advantageous.

As a consequence of the absence of a surface charge the pigments thus produced are frequently insufficiently suspendable. The dispersibility can be dramatically enhanced by aftercoating with an organosilane. The silane coating is carried out immediately following the $Ce_2O_3/TiO_2$/colloid coating. Suitable silane compounds include organofunctional silanes of the formula $$Y-(CH_2)_n-SiX_3$$

where

Y is $H_2N-$, $CH_2=CH-$, $CH_2=C(CH_3)-COO-$, $H_2C(\overset{O}{\diagup\diagdown})CH-CH_2O-$, $H_2N-CH_2-CH_2-NH-$, $HS-$, $Cl-$, $\begin{matrix}H_2C-N\\ |\phantom{xx}\diagdown\\ |\phantom{xxx}C-\\ |\phantom{xx}\diagup\phantom{/}\\ H_2C-N\end{matrix}$ X is $OCH_3$, $OC_2H_5$, OR, Cl, $-OCOCH_3$ R is alkyl having 1–6 carbon atoms n is 0–3.

Preference is given to using aminosilanes. The silane proportion is 0.5–10% by weight, preferably 1–5% by weight, in particular 1–3% by weight, based on the total pigment.

In place of the organofunctional silane compounds it is also possible to use the abovementioned colloidal particles in amounts from 0.1 to 10% by weight, preferably from 0.5 to 5% by weight. It is also possible to use mixtures of organofunctional silane compounds and colloidal particles in any mixing ratio. Preference is given to using aminosilanes, gelatin, cellulose and starch.

This aftercoating, which is carried out immediately following the metal salt hydrolysis and colloid precipitation, has the effect that, following calcination in an inert gas atmosphere, a carbon layer forms on the pigment surface, whereas occluded carbon particles are present in the titanium dioxide layer.

The $TiO_2$ pigments thus produced, which are produced in a one-pot process, have after calcination, because of the cerium(III) content, an enhanced photostability and a very good dispersibility, in particular in aqueous systems, as a result of the silane and/or colloid aftercoating.

The pigments produced according to the invention are abrasion-resistant, so that they can be used for various purposes, in particular for automotive coatings, for printing inks and also in cosmetics.

The present invention thus also provides for the use of the carbon-containing pigments in formulations such as paints, coatings, printing inks, plastics and cosmetics.

The invention also provides formulations comprising the pigments of the invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P 44 10 990.3 and P 44 35 300.6, are hereby incorporated by reference. DE-A-41 25 134 and DE-C-2 557 796 correspond to U.S. Pat. No. 5,271,771 and U.S. Pat. No. 4,076,555, respectively.

EXAMPLE 1

1% of SnO$_2$+4% of gelatin+38.6% of TiO$_2$ on mica 100 g of mica of the particle size 10–60 μm are suspended in 2 l of water and heated to 75° C. To the mica suspension is metered a solution consisting of 2.3 g of SnCl$_4$×5H$_2$O, 50 ml of water and 10 ml of 5% HCl. The pH is kept constant with 32% NaOH solution during the addition. On completion of the addition of the SnCl$_4$ solution, the batch is additionally stirred for 0.5 h at 75° C. and pH 1.8 to complete the precipitation reaction. Then 250 ml of TiCl$_4$ solution (368 g TiCl$_4$/l of water) and the gelatin solution (4 g dissolved in 170 ml of water) are metered simultaneously but separately to the pigment suspension.

The pH is kept constant with 32% NaOH solution during the addition. On attainment of the desired silvery hue, the addition of the TiCl$_4$ solution (~250 ml) is discontinued. Then the batch is stirred at 75° C. for 15 min. 32% NaOH solution is used to adjust the pH to 6.5 and the pigment suspension is once more stirred for 15 min without heat treatment. The pigment suspension is allowed to sediment and after 1.5 h the supernatant solution is sucked off. Finally, the pigment is washed salt-free, dried at 140° C. for 18 h and calcined in a nitrogen atmosphere at 850° C. for 45 min.

EXAMPLE 2

Example 1 is repeated to coat 100 g of mica with SnO$_2$, TiO$_2$ and 4 g of dextrin (starch gum from Merck, Darmstadt).

EXAMPLE 3

Example 1 is repeated to coat 100 g of mica of the particle size 10–60 μm with SnO$_2$, TiO$_2$ and 4 g of Mowiol (polyvinyl alcohol from Hoechst, Frankfurt).

EXAMPLE 4

SnO$_2$+Ce$_2$O$_3$+gelatin+TiO$_2$+silane on mica 100 g of mica of the particle size 10–60 μm are suspended in 2 l of water and heated to 75° C. To the mica suspension is metered a solution consisting of 2.3 g of SnCl$_4$×5 H$_2$O, 50 ml of water and 10 ml of 37% HCl. The pH is kept constant with 32% NaOH solution during the addition. On completion of the addition of the SnCl$_4$ solution, the batch is additionally stirred for 0.5 h at 75° C. and pH 1.8 to complete the precipitation reaction. Then a solution consisting of 1.14 g of CeCl$_3$.7H$_2$O and 20 ml of water is added with stirring. Thereafter 250 ml of TiCl$_4$ solution (368 g of TiCl$_4$/l of water) and the gelatin solution/4 g dissolved in 170 ml of water) are metered simultaneously but separately to the pigment suspension. The pH is kept constant with 32% NaOH solution during the addition. On attainment of the desired silvery hue, the addition of the TiCl$_4$ solution (~250 ml) is discontinued. Then the batch is stirred at 75° C. for 15 min. 32% NaOH solution is used to adjust the pH to 6.0 and the pigment suspension is stirred once more for 5 min without heat treatment. Then a 2% aqueous silane solution (2 g of Z6040 from Hüls AG, Marl, in 100 ml of H$_2$O) is added in the course of a minute and the batch is stirred for 15 minutes. The pigment suspension is allowed to sediment and after 1.5 h the supernatant solution is sucked off. Finally, the pigment is washed salt-free, dried at 140° C. for 18 h and calcined in a nitrogen atmosphere at 850° C. for 45 min.

EXAMPLE 5

Example 4 is repeated to coat 100 g of mica with SnO$_2$, Ce$_2$O$_3$, TiO$_2$ and 4 g of gelatin. As a last step a 0.5% gelatin solution (0.5 g of gelatin dissolved in 100 ml of water) is added to the pigment suspension in the course of a minute and the pigment suspension is stirred for 15 minutes. The working-up is carried out analogously to Example 4.

EXAMPLE 6

Example 4 is repeated to coat 100 g of mica of particle size 10–60 μm with SnO$_2$, Ce$_2$O$_3$, TiO$_2$, Mowiol (polyvinyl alcohol from Hoechst, Frankfurt) and 2% of silane.

EXAMPLE 7

Example 4 is repeated to coat 100 g of mica of particle size 10–60 μm with SnO$_2$, C$_2$O$_3$, TiO$_2$, Mowiol (polyvinyl alcohol from Hoechst, Frankfurt). Instead of the 2% silane solution, a 0.5% Mowiol solution is used for the aftercoating. The working-up is carried out analogously to Example 4.

EXAMPLE 8

Example 4 is repeated to coat 100 g of mica of particle size 10–60 μm with SnO$_2$, Ce$_2$O$_3$, TiO$_2$, dextrin (starch rubber from E. Merck, Darmstadt) and 2% of silane.

EXAMPLE 9

Example 4 is repeated to coat 100 g of mica of particle size 10–60 μm with SnO$_2$, Ce$_2$O$_3$, TiO$_2$, dextrin (starch rubber from E. Merck, Darmstadt). Then a 0.5% aqueous dextrin solution (5 g of dextrin in 100 ml of water) is added in the course of a minute and the batch is stirred for 15 minutes. The working-up is carried out as described in Example 4.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Carbon-containing pigments prepared by pyrolysis of substrates with a layer consisting of one or more metal oxides, colloidal organic particles and optionally an organofunctional silane compound at temperatures >700° C. under oxygen-free conditions.

2. Carbon-containing pigments according to claim 1, characterized in that the substrates are platelet-shaped.

3. Carbon-containing pigments prepared by pyrolysis of platelet-shaped substrates with a layer consisting of one or metal oxides, colloidal organic particles and, optionally, an organofunctional silane compound at temperatures greater than 700° C. under oxygen-free conditions.

4. Carbon-containing pigments according to claim 1, characterized in that the colloidal organic particles are starch, cellulose, gelatin or derivatives thereof.

5. Carbon-containing pigments according to claim 1, characterized in that the organofunctional silane compound is a compound of the formula

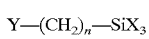

wherein

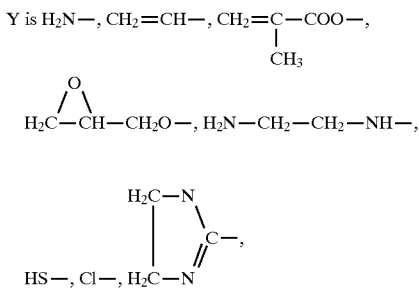

X is $OCH_3$, $OC_2H_5$, OR, Cl, $-OCOCH_3$,
R is alkyl having 1–6 carbon atoms, and
n is 0–3.

6. Process for producing carbon-containing pigments by pyrolyzing a substrate with a layer consisting of one or more metal oxides and colloidal organic particles and optionally an organofunctional silane compound at temperatures >700° C. under oxygen-free conditions, characterized in that an aqueous substrate suspension is prepared and admixed simultaneously with at least one hydrolyzable metal salt solution and separately with an aqueous organic colloid solution, wherein the substrate suspension has a value for pH being maintained in a range which causes the metal salt to hydrolyze, and the substrate coated in this way optionally has added to it an aftercoating of organofunctional silane compound and the coated substrate is separated off, washed, dried and calcined at temperatures greater than 700° C. under oxygen-free conditions.

7. Process according to claim 6, characterized in that the metal salt is a titanium salt and a cerium(III) salt.

8. A method of using carbon-containing pigments which comprises incorporating carbon-containing pigments according to claim 1 into a formulation selected from the group consisting of paints, coatings, other than paints, printing inks, plastics and cosmetics.

9. A formulation comprising carbon-containing pigments obtainable by pyrolysis of substrates with a layer consisting of one or more metal oxides, colloidal organic particles and optionally an organofunctional silane compound at temperatures >700° C. under oxygen-free conditions.

10. Carbon-containing pigments obtainable by pyrolysis of substrates with a first layer consisting of one or more metal oxides, colloidal organic particles and optionally an organofunctional silane compound at temperatures >700° C. under oxygen free conditions.

11. Carbon-containing pigments obtainable by pyrolysis of substrates with a layer consisting of one or more metal oxides, colloidal organic particles selected from the group consisting of starch, cellulose, gelatin and derivatives thereof; and optionally an organofunctional silane compound at temperatures >700° C. under oxygen-free conditions.

* * * * *